(12) United States Patent
Kristen et al.

(10) Patent No.: US 6,946,568 B2
(45) Date of Patent: Sep. 20, 2005

(54) COMPLEXED COMPOUNDS AND USE THEREOF FOR THE POLYMERIZATION OF OLEFINS

(75) Inventors: Marc Oliver Kristen, Limburgerhof (DE); Benno Bildstein, Innsbruck (AT); Alexander Krajete, Salzburg (AT)

(73) Assignee: Basell Polyolefine GmbH, Wesseling (DE)

(*) Notice: Subject to any disclaimer, the term of this patent is extended or adjusted under 35 U.S.C. 154(b) by 17 days.

(21) Appl. No.: 10/467,169

(22) PCT Filed: Feb. 6, 2002

(86) PCT No.: PCT/EP02/01191

§ 371 (c)(1),
(2), (4) Date: Aug. 13, 2003

(87) PCT Pub. No.: WO02/064644

PCT Pub. Date: Aug. 22, 2002

(65) Prior Publication Data

US 2004/0077890 A1 Apr. 22, 2004

(30) Foreign Application Priority Data

Feb. 13, 2001 (DE) .......................... 101 07 045

(51) Int. Cl.⁷ .............................. C07F 7/00; C07F 9/00; B01J 31/00; C08F 4/44
(52) U.S. Cl. .......................... 556/53; 556/42; 502/103; 502/117; 502/152; 502/155; 502/156; 502/172; 526/161; 526/172
(58) Field of Search .................... 556/42, 53; 502/103, 502/117, 152, 155, 156, 172; 526/161, 172

(56) References Cited

U.S. PATENT DOCUMENTS

| 6,309,997 B1 | * | 10/2001 | Fujita et al. | 502/167 |
| 6,451,728 B1 | * | 9/2002 | Matsui et al. | 502/167 |
| 6,459,005 B1 | * | 10/2002 | Hirano et al. | 585/12 |

FOREIGN PATENT DOCUMENTS

| DE | 100 17 663 | 10/2001 |
| DE | 100 35 654 | 1/2002 |
| EP | 0 803 520 | 10/1997 |
| EP | 0 874 005 | 10/1998 |
| EP | 1 174 442 | 1/2002 |
| JP | 2000-230010 | * 8/2000 |
| JP | 2000-313712 | * 11/2000 |
| WO | 96/23010 | 8/1996 |
| WO | 98/27124 | 6/1998 |
| WO | 02 02573 | 1/2002 |

OTHER PUBLICATIONS

H.H. Brintzinger et al., Angew. Chem., vol. 107, pp. 1255–1283, 1995.
G.J.P. Britovsek et al., Angew. Chem., pp. 449–468 1999.
G.J.P. Britovsek et al, Angew. Chem. Int. Ed. Engl., vol. 38, pp. 429–447, 1999.
Bei Xiaohong et al, Organometallics, vol. 16, pp. 3282–3302, 1997.
T. Tsukahara et al., Organometallics, vol. 16, pp. 3303–3313, 1997.
I. Kim et al., Organometallics, vol. 16, pp. 3314–3323, 1997.

* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT

Complexes of the formulae Ia and Ib

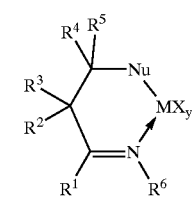

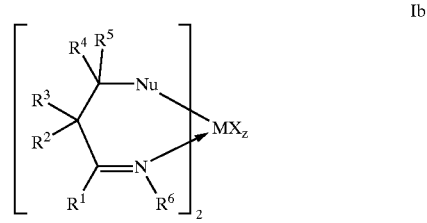

where M=Ti, Zr, Hf, V, Nb or Ta, can be used for the polymerization and copolymerization of olefins, for example in suspension polymerization processes, gas-phase polymerization processes and bulk polymerization processes.

13 Claims, No Drawings

COMPLEXED COMPOUNDS AND USE THEREOF FOR THE POLYMERIZATION OF OLEFINS

The present invention relates to complexes of the formulae Ia and Ib,

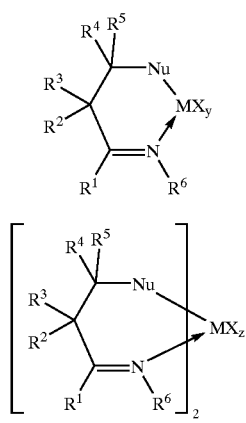

where the variables are defined as follows:
Nu is selected from among O, S and N—$R^7$;
M is selected from among Ti, Zr, Hf, V, Nb and Ta;
y corresponds to the oxidation state of M minus 1;
z corresponds to the oxidation state of M minus 2;
X are identical or different and are selected from among halogen, $C_1$–$C_8$-alkyl, $C_3$–$C_{12}$-cycloalkyl, $C_7$–$C_{13}$-aralkyl and $C_6$–$C_{14}$-aryl,
$R^1$ to $R^7$ are identical or different and are selected from among
  hydrogen,
  $C_1$–$C_{18}$-alkyl, substituted or unsubstituted,
  $C_2$–$C_{18}$-alkenyl, substituted or unsubstituted, having from one to 4 isolated or conjugated double bonds;
  $C_3$–$C_{12}$-cycloalkyl, substituted or unsubstituted,
  $C_7$–$C_{13}$-aralkyl,
  $C_6$–$C_{14}$-aryl, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^8R^9R^{10}$ and $O$—$SiR^8R^9R^{10}$;
  five- and six-membered nitrogen-containing heteroaryl radicals, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^8R^9R^{10}$ and $O$—$SiR^8R^9R^{10}$;
where adjacent radicals $R^1$ to $R^6$ may be joined to one another or to $R^7$ to form a 5- to 12-membered ring which may in turn bear substituents selected from among $C_1$–$C_8$-alkyl, substituted or unsubstituted, $C_2$–$C_8$-alkenyl, substituted or unsubstituted and having from one to 4 isolated or conjugated double bonds, $C_3$–$C_{12}$-cycloalkyl, substituted or unsubstituted, $C_7$–$C_{13}$-aralkyl and $C_6$–$C_{14}$-aryl;
$R^8$ to $R^{10}$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

The present invention also relates to a process for the polymerization of olefins using complexes of the formulae Ia and Ib.

Polymers and copolymers of olefins are of great economic importance because the monomers are readily available in large quantities and because the polymers can be varied within a wide range by variation of the method of preparation or the processing parameters. The catalyst used is of particular significance in the process for preparing the polymers. Apart from Ziegler-Natta catalysts, various single-site catalysts are of increasing importance. In the latter, central atoms which have been examined in some detail include not only Zr as in, for example, metallocene catalysts (H.-H. Brintzinger et al., *Angew. Chem.* 1995, 107, 1255) but also Ni or Pd (WO 96/23010) or Fe and Co (e.g. WO 98/27124). The complexes of Ni, Pd, Fe and Co are also referred to as complexes of late transition metals.

Metallocene catalysts have disadvantages for industrial use. The most frequently employed metallocenes, namely zirconocenes and hafnocenes, are sensitive to hydrolysis. In addition, most metallocenes are sensitive to many catalyst poisons such as alcohols, ethers and CO, which makes it necessary for the monomers to be carefully purified.

While Ni and Pd complexes (WO 96/23010) catalyze the formation of highly branched polymers which are of little commercial interest, the use of Fe or Co complexes leads to formation of highly linear polyethylene containing very low proportions of comonomer. EP-A 0 874 005 discloses further polymerization-active complexes. These complexes are preferably Ti complexes with salicylaldimine ligands. These, too, bear phenyl substituents or substituted phenyl substituents on the aldimine nitrogen (pages 18–23), or else the aldimine nitrogen is incorporated in a 6-membered ring (pages 31–32). However, they generally produce low molecular weight polyethylenes which are not very suitable as materials. Furthermore, all the ligands disclosed in EP-A 0 874 005 have the oxygen atom as part of a phenolic system, which restricts the choice of readily available starting materials.

As G. J. P. Britovsek et al. show in Angew. Chem. 1999, 111, 448 and Angew. Chem. Int. Ed. Engl. 1999, 38, 428, the search for very versatile polymerization-active complexes continues to be of importance because of the great commercial importance of polyolefins. Particular attention has been attracted by complexes of the early transition metals with bidentate ligands, for example complexes of the formula A,

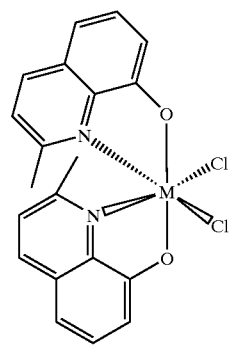

which have been examined by X. Bei et al. in Organometallics 1997, 16, 3282. However, the activities of the complexes in which M=Ti or Zr in the polymerization of ethylene were too low for the complexes to be of commercial interest. T. Tsukahara et al. in Organometallics 1997, 16, 3303 and I. Kim et al. in Organometallics 1997, 16, 3314 have examined β-hydroxypyridyl complexes of the formula B

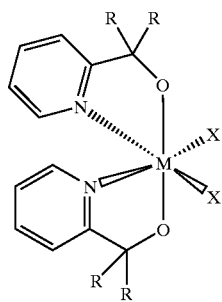

and their activity in the polymerization of ethylene. If, for example, R are each selected from among $CH_3$ and $CF_3$ and X is benzyl or neopentyl, only an extremely low polymerization activity, if any, opposite ethylene could be observed when the complex was activated with trispentafluorophenylborane. On the other hand, if R=para-tert-butylphenyl and X=benzyl, a low activity was observed, but this was too low for commercial purposes. In addition, the polymers prepared in this way had a molecular weight $M_n$ of 6200 g which is too low for materials.

It is therefore an object of the invention
to provide new complexes which are suitable for the polymerization of olefins to give high molecular weight polymers;
to provide a process for preparing the complexes of the present invention;
to provide a process for the polymerization or copolymerization of olefins using the complexes of the present invention;
to provide supported catalysts for the polymerization of olefins and a process for preparing the supported catalysts of the present invention using the complexes of the present invention; and
to polymerize and copolymerize olefins using the supported catalysts of the present invention.

We have found that this object is achieved by means of complexes having the structures of the formulae Ia and Ib defined at the outset.

In formula I, the variables are defined as follows:
Nu is selected from among O, S and N—$R^7$, with oxygen being preferred;
M is selected from among Ti, Zr, Hf, V, Nb and Ta in the oxidation states from +3 to +5; preferably Ti or Zr and particuarly preferably Zr;
y corresponds to the oxidation state of M minus 1,
z corresponds to the oxidation state of M minus 2, where M can be a metal in the highest oxidation state but does not have to be;
X are identical or different and are selected from among
halogen, such as fluorine, chlorine, bromine and iodine, with preference being given to chlorine or bromine and particular preference being given to chlorine;
$C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl; and $C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

X is preferably halogen.
$R^1$ to $R^7$ are identical or different and are selected from among hydrogen,
$C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isopropenyl, 1-isoprenyl, α-styryl, β-styryl, 1-cis-1,2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5- dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl substituted by one or more identical or different substituents selected from among $C_1$–$C_{18}$-alkyl groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: monohalogenated or polyhalogenated $C_1$–$C_{18}$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isopropenyl, 1-isoprenyl, α-styryl, β-styryl, 1-cis-1, 2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group;

five and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- and six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl substituted by one or more identical or different substituents selected from among $C_1$–$C_{18}$-groups such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl, preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted C₁–C₈-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isopropenyl, 1-isoprenyl, α-styryl, β-styryl, 1-cis-1, 2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups and particular preference being given to the trimethylsilyl group and the tert-butyldimethylsilyl group;

silyloxy groups $OSiR^8R^9R^{10}$, where $R^8$ to $R^{10}$ are selected independently from among hydrogen, $C_1$–$C_8$-alkyl groups, benzyl radicals and $C_6$–$C_{14}$-aryl groups; with preference being given to the trimethylsilyloxy, triethylsilyloxy, triisopropylsilyloxy, diethylisopropylsilyloxy, dimethylthexylsilyloxy, tert-butyldimethylsilyloxy, tert-butyldiphenylsilyloxy, tribenzylsilyloxy, triphenylsilyloxy and tri-para-xylylsilyloxy groups and particular preference being given to the trimethylsilyloxy group and the tert-butyldimethylsilyloxy group In a particularly preferred embodiment, $R^2$ or $R^3$ is different from hydrogen.

In a particlar embodiment, adjacent radicals $R^1$ to $R^6$ of the complexes of the formulae Ia and Ib may be joined to one another or to $R^7$ to form a 5- to 12-membered ring. For example, $R^1$ and $R^2$ may together be: —(CH₂)₃— (trimethylene), —(CH₂)₄— (tetramethylene), —(CH₂)₅— (pentamethylene), —(CH₂)₆— (hexamethylene), —CH₂—CH=CH—, —CH₂—CH=CH—CH₂—, —CH=CH—CH=CH—, —O—CH₂—O—, —O—CHMe—O—, —O—CH—(C₆H₅)—O—, —O—CH₂—CH₂—O—, —O—CMe₂—O—, —NMe—CH₂—CH₂—NMe—, —NMe—CH₂—NMe— or —O—SiMe₂—O— where Me=CH₃. In a further embodiment of the present invention, $R^1$ and $R^6$ are joined to one another to form a 5- to 12-membered ring. In a preferred embodiment, $R^1$ and $R^6$ are joined by a substituted or unsubstituted —CH=CH—CH=CH— unit.

The complexes required for the process of the present invention can be synthesized readily.

The synthesis of the novel complexes of the formulae Ia and Ib generally starts out from a ligand of the formula II,

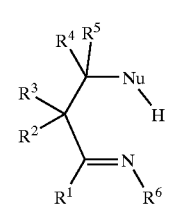

II where the variables are as defined above.

The ligands of the formula II are firstly deprotonated by means of a base and subsequently reacted with metal compounds of the formula $MX_{y+1}$.

Bases which can be used are the metal alkyls customary in organometallic chemistry, for example methyllithium, ethyllithium, n-butyllithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are, for example, toluene, ortho-xylene, meta-xylene, para-xylene, ethylbenzene or mixtures of these, also acyclic or cyclic ethers such as 1,2-dimethoxyethane, tetrahydrofuran or diethyl ether.

This deprotonation is generally complete after a few hours; it is appropriate to employ a reaction time of from 2 to 10 hours, preferably from 3 to 5 hours. The temperature conditions are generally not critical; temperatures of from −90° C. to −20° C. are preferred for the deprotonation.

The deprotonated ligand and the metal compound of the formula $MX_{y+1}$ are subsequently reacted with one another.

$MX_{y+1}$ can optionally be stabilized by uncharged ligands. Possible uncharged ligands are the customary ligands of coordination chemistry, for example cyclic and acyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphine.

The conditions for the reaction are not critical per se; it is usual to mix the deprotonated ligand II and $MX_{y+1}$ with one another in a suitable solvent such as benzene, toluene, ethylbenzene, ortho-xylene, meta-xylene or para-xylene, chlorobenzene, cyclohexane, methylene chloride or a mixture of these. The temperature can be in the range from −100° C. to +150° C., preferably from −78° C. to +100° C.

The reaction temperature should not be less than the melting point of the solvent; temperatures above the boiling point of the solvent concerned can be achieved in an autoclave. It is important that the reaction is carried out in the absence of oxygen and moisture.

The molar ratio of ligand to M can be in the range from 5:1 to 1:5. However, since the ligands of the formula II are more difficult to obtain than the metal compounds, molar ratios of ligand:M in the range from 1:1 to 1:3 are preferred. Particular preference is given to stoichiometric amounts.

However, if compounds of the formula Ib are to be obtained, molar ratios of ligand:M of from 2:1 to 4:1 are preferred.

The novel complexes of the formulae Ia and Ib can be purified by the methods customary in organometallic chemistry, with particular preference being given to crystallization and precipitation. Filtration via filter aids such as Celite® is also useful.

The ligands of the formula II are prepared by deprotonation of an imine of the formula III,

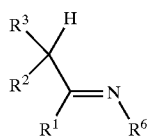

III which bears an acidic α-H atom and subsequent reaction with an electrophilic compound of the formula IV,

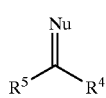

IV where the variables in the compounds III and IV are as defined above.

Bases which can be used are the metal alkyls customary in organometallic chemistry, for example methyllithium, ethyllithium, n-butyl lithium, sec-butyllithium, tert-butyllithium or hexyllithium, also Grignard compounds such as ethylmagnesium bromide, also lithium amide, sodium amide, potassium amide, potassium hydride or lithium diisopropylamide ("LDA"). Solvents which have been found to be useful are, for example, toluene, ortho-xylene, meta-xylene, para-xylene, ethylbenzene or mixtures of these, also acyclic or cyclic ethers such as 1,2-dimethoxyethane, tetrahydrofuran or diethyl ether.

This deprotonation is generally complete after from some minutes to a few hours; it is appropriate to employ a reaction time of from 30 minutes to 10 hours, preferably from 1 to 5 hours. The temperature conditions are generally not critical; temperatures of from −90° C. to +30° C.

The deprotonated imine III and the electrophilic compound IV are subsequently reacted with one another.

The conditions for the reaction are not critical per se; it is usual to mix the deprotonated imine III and the electrophilic compound IV with one another in a suitable solvent such as benzene, toluene, ethylbenzene, ortho-xylene, meta-xylene or para-xylene, chlorobenzene, cyclohexane, methylene chloride or a mixture of these. The temperature can be in the range from −100° C. to +150° C., preferably from −78° C. to +100° C. The reaction temperature should not be less than the melting point of the solvent; temperatures above the boiling point of the solvent concerned can be achieved in an autoclave. It is important that the reaction is carried out in the absence of oxygen and moisture.

The molar ratio of III to IV can be in the range from 5:1 to 1:5. Preference is given to molar ratios of III:IV in the range from 3:1 to 1:3 and particular preference is given to stoichiometric amounts.

The synthesis of the imines of the formula II can be carried out by various methods which are known per se from the literature. Examples which may be mentioned are: B. Bildstein et al., Synthesis 1994, 2, 157; W. Flitsch et al., Chem. Ber. 1969, 102, 3268; A. Cobas et al., J. Org. Chem. 1993, 58, 3113; M. Sato, et al., Chem. Lett. 1992, 3, 485; Reddelien, Chem. Ber. 1910, 43, 2478, P. Schnider et al., Chem. Eur. J. 1997, 3, 887.

It has been found that the novel complexes of the formulae Ia and Ib are suitable for polymerizing olefins. They are particularly useful for polymerizing and copolymerizing ethylene and propylene to form high molecular weight polymers. Complexes of the formula Ib are chiral and can produce isotactic polypropylene in the polymerization of propylene.

For the novel complexes of the formulae Ia and Ib to be catalytically active, they have to be activated. Suitable activators are selected aluminum and boron compounds bearing electron-withdrawing radicals (e.g. trispentafluorophenylborane, trispentafluorophenyl-aluminum, N,N-dimethylanilinium tetrakispentafluoro-phenylborate, tri-n-butylammonium tetrakispentafluoro-phenylborate, N,N-dimethylanilinium tetrakis(3,5-bisperfluoromethyl)phenylborate, tri-n-butylammonium tetrakis(3,5-bisperfluoromethyl)phenylborate and tritylium tetrakispentafluorophenylborate). Preference is given to dimethylanilinium tetrakispentafluorophenylborate, tritylium tetrakispentafluorophenylborate and trispentafluorophenylboran.

If boron or aluminum compounds are used as activators for the novel complexes of the formulae Ia and Ib, they are generally used in a molar ratio of from 1:10 to 10:1, based on M. They are preferably used in a ratio of from 1:2 to 5:1 and particularly preferably in stoichiometric amounts.

Another suitable class of activators consists of aluminoxanes. The structure of the aluminoxanes is not known precisely. They are products which are obtained by careful partial hydrolysis of aluminum alkyls (cf. DE-A 30 07 725). These products are not in the form of pure chemical compounds, but as mixtures of open-chain and cyclic structures of the types VIa and VIb. These mixtures are presumably in dynamic equilibrium.

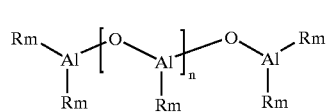

Va

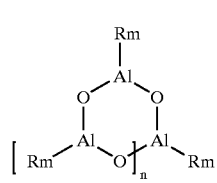

Vb

In the formulae Va and Vb, the radicals R''' are each, independently of one another, $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl, preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl, preferably cyclopentyl, cyclohexyl or cycloheptyl;

$C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, or $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 1 to 25 and particularly preferably from 2 to 22.

Cage-like structures for aluminoxanes are also discussed in the literature (Y. Koide, S. G. Bott, A. R. Barron Organometallics 1996, 15, 2213–26; A. R. Barron Macromol. Symp. 1995, 97, 15–25). Regardless of the actual structure of the aluminoxanes, they are suitable as activators for the novel metal complexes of the formulae Ia and Ib.

Mixtures of various aluminoxanes are particularly preferred activators in cases when the polymerization is carried out in a solution in a paraffin, for example n-heptane or isododecane. A particularly preferred mixture is the CoMAO available commercially from Witco GmbH, which has the formula $[(CH_3)_{0.9}(iso-C_4H_9)_{0.1}AlO]_n$.

To activate the complexes of the formulae Ia and Ib by means of aluminoxanes, an excess of aluminoxane, based on M, is generally necessary. Appropriate molar ratios of M:Al are in the range from 1:10 to 1:10,000, preferably from 1:50 to 1:1000 and particularly preferably from 1:100 to 1:500.

The chosen complex of the formula Ia or Ib and the activator together form a catalyst system.

The activity of the catalyst system of the invention can be increased by addition of further aluminum alkyl of the formula $Al(R''')_3$ or aluminoxanes; aluminum alkyls of the formula $Al(R''')_3$ or aluminoxanes can also act as molar mass regulators. A further effective molar mass regulator is hydrogen. The molar mass can be regulated particularly effectively via the reaction temperature and the pressure. If a boron compound as described above is to be used, the addition of an aluminum alkyl of the formula $Al(R''')_3$ is particularly preferred.

Pressure and temperature conditions during the polymerization can be chosen within wide limits. Pressures in a range from 0.5 bar to 4000 bar have been found to be useful; preference is given to from 10 to 75 bar or high-pressure conditions of from 500 to 2500 bar. A suitable temperature range has been found to be from 0 to 120° C., preferably from 40 to 100° C. and particularly preferably from 50 to 85° C.

As monomers, mention may be made of the following olefins: ethylene, propylene, 1-butene, 1-pentene, 1-hexene, 1-octene, 1-decene and 1-undecene, with propylene and ethylene being preferred and ethylene being particularly preferred.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Solvents which have been found to be suitable are toluene, ortho-xylene, meta-xylene, para-xylene and ethylbenzene and also mixtures of these, also, under high-pressure conditions, supercritical ethylene.

The catalyst systems of the present invention polymerize olefins to give polyolefins having a very high molecular weight.

Hydrogen has been found to be an effective chain transfer agent in polymerizations using the catalyst systems of the invention, i.e. the molecular weight of the polymers obtainable by means of the catalyst system of the present invention can be reduced by addition of hydrogen. If sufficient hydrogen is added, waxes are obtained. The hydrogen concentration required for this depends, inter alia, on the type of polymerization plant employed.

For the catalyst systems of the present invention to be able to be used in modern polymerization processes such as suspension processes, bulk polymerization processes or gas-phase processes, they have to be immobilized on a solid support. Otherwise, morphology problems with the polymer (lumps, deposits on walls, blockages in lines or heat exchangers) can occur and force shutdown of the plant. Such an immobilized catalyst system will be referred to as a catalyst.

The catalyst systems of the present invention can be deposited on solid support materials. Suitable support materials are, for example, porous metal oxides of metals of groups 2 to 14 or mixtures thereof, also sheet silicates and zeolites. Preferred examples of metal oxides of groups 2 to 14 are $SiO_2$, $B_2O_3$, $Al_2O_3$, MgO, CaO and ZnO. Preferred sheet silicates are montmorillonites and bentonites; the preferred zeolite is MCM-41.

Particularly preferred support materials are spherical silica gels and aluminosilicate gels of the formula $SiO_2 \cdot a\, Al_2O_3$, where a is generally from 0 to 2, preferably from 0 to 0.5. Such silica gels are commercially available, e.g. silica gel SG 332, Sylopol® 948 or 952 or S 2101 from W. R. Grace or ES 70X from Crosfield.

As regards the particle size of the support material, mean particle diameters which have been found to be useful are from 1 to 300 μm, preferably from 20 to 80 μm, determined by known methods such as sieve methods. The pore volume of these supports is from 1.0 to 3.0 ml/g, preferably from 1.6 to 2.2 ml/g and particularly preferably from 1.7 to 1.9 ml/g. The BET surface area is from 200 to 750 m$^2$/g, preferably from 250 to 400 m$^2$/g.

To remove impurities, in particular moisture, adhering to the support material, the support materials can be baked before doping, with temperatures of from 45 to 1000° C. being suitable. Temperatures of from 100 to 750° C. are particularly useful for silica gels and other metal oxides. This baking can be carried out for from 0.5 to 24 hours, preferably from 1 to 12 hours. The pressure conditions depend on the process chosen; baking can be carried out in a fixed-bed process, a stirred vessel or else in a fluidized-bed process. Baking can in general be carried out at atmospheric pressure. However, reduced pressures of from 0.1 to 500 mbar are advantageous, a range from 1 to 100 mbar is particularly advantageous and a range from 2 to 20 mbar is very particularly advantageous. In the case of fluidized-bed processes, on the other hand, it is advisable to employ a slightly superatmospheric pressure in a range from 1.01 bar to 5 bar, preferably from 1.1 to 1.5 bar.

Chemical treatment of the support material with an alkyl compound such as an aluminum alkyl, a lithium alkyl or an aluminoxane is likewise possible.

In the case of a suspension polymerization process, use is made of suspension media in which the desired polymer is insoluble or soluble to only a slight extent, because otherwise deposits of products occur in the parts of the plant in which the product is separated off from the suspension medium and force repeated shutdowns and cleaning operations. Suitable suspension media are saturated hydrocarbons such as propane, n-butane, isobutane, n-pentane, isopentane, n-hexane, isohexane and cyclohexane, with isobutane being particularly preferred.

Pressure and temperature conditions during the polymerization can be chosen within wide limits. A suitable pressure range has been found to be from 0.5 bar to 150 bar, preferably from 10 to 75 bar. A suitable temperature range has been found to be from 0 to 120° C., preferably from 40 to 100° C.

As monomers, mention may be made of the following olefins: ethylene, propylene, 1-butene, 1-pentene, 1-hexene, 1-octene, 1-decene and 1-undecene.

Suitable comonomers are α-olefins, for example from 0.1 to 20 mol % of 1-butene, 1-pentene, 1-hexene, 4-methyl-1-pentene, 1-octene, 1-decene or 1-undecene. Further suitable comonomers are isobutene and styrene, also internal olefins such as cyclopentene, cyclohexene, norbornene and norbornadiene.

Furthermore, hydrogen has been found to be an effective chain transfer agent in polymerizations using the catalysts of the invention, i.e. the molecular weight of the polymers obtainable by means of the catalysts of the present invention can be reduced by addition of hydrogen. If sufficient hydrogen is added, waxes are obtained. The hydrogen concentration required for this depends, inter alia, on the type of polymerization plant employed. Addition of hydrogen increases the activity of the catalysts of the present invention.

The catalysts of the present invention can also be used together with one or more other polymerization catalysts known per se. Thus, they can be used together with Ziegler-Natta catalysts, supported metallocene catalysts containing transition metals of groups 4 to 6 of the Periodic Table of the Elements, catalysts based on late transition metals (WO 96/23010), Fe or Co complexes with pyridyldiimine ligands, as are disclosed in WO 98/27124 or chromium oxide catalysts of the Phillips type.

If a plurality of catalysts is used, it is possible to mix various catalysts with one another and to meter them in together or to use cosupported complexes on a common support or else to meter various catalysts separately into the polymerization vessel at the same point or at various points.

The following examples illustrate the invention.

General preliminary remarks:

All work was, unless indicated otherwise, carried out with exclusion of air and moisture using standard Schlenk techniques. Apparatus and chemicals were prepared accordingly. The polymer viscosity was determined in accordance with ISO 1628-3.

1. Preparation of the Ligands 1.1 Preparation of the Imines

The imines were prepared by 3 methods, depending on the reactivity of the starting materials used:

1st method: the starting materials, viz. 4.97 g of acetophenone (41.4 mmol), 7.33 g of 2,6-diisopropylaniline (41.4 mmol), were placed in a 250 ml round-bottom flask fitted with a water separator, dissolved in 70 ml of toluene and, after addition of 500 mg of p-toluenesulfonic acid, refluxed for 2 hours. The orange solution was washed twice with H$_2$O, then once with 10% NaHCO$_3$ solution to make it neutral. The organic phase was dried over Na$_2$SO$_4$. After the solvent had been taken off on a rotary evaporator, traces of toluene and unreacted amine and ketone were taken off in a high vacuum at from 105 to 115° C. The oily imine crystallized overnight.

This method was used to prepare: imine III.1

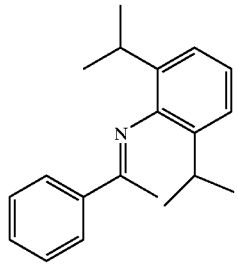

III.1

Yield: 84.6%, empirical formula: C$_{20}$H$_{25}$N, color: yellow, m.p.: 68–69° C.

1H NMR (CDCl$_3$): 1.21 (12H, m, 4×CH$_3$), 2.16 (3H, S, CH$_3$), 2.83 (2H, sept., CH), 7.11–8.12 (8H, m, phenyl)

13C NMR (CDCl$_3$): 18.0, 22.9, 23.2, 28.2, 122.9, 123.3, 127.1, 128.4, 130.3, 136.0, 139.1, 146.7, 164.7 (C=N)

IR (KBr, cm$^{-1}$): 3056 (w), 2958 (m), 2867 (m), 1630 (s), 1578 (s), 1449 (s), 1366 (m), 1289 (s), 1243 (m), 1192 (m), 1111 (w), 1044 (w), 1027 (m), 969 (w), 938 (m), 822 (m), 774 (vs), 760 (vs), 735 (s), 693 (vs) M$^+$=279.2 m/e

2nd method: the starting materials, viz. 0.19 g of N-aminopyrrole (2.3 mmol), 0.28 g of acetophenone (2.3 mmol), were placed in a 50 ml round-bottomed flask, dissolved in 1 ml of ethanol and, after addition of 3 drops of formic acid, stirred at room temperature for 30 minutes. Distilling off the solvent and the formic acid gave the whiteish yellow imine in high purity.

This method was used to prepare: imine III.2 (as described by W. Flitsch et al., Chem. Ber. 1969, 102, 3268–3276).

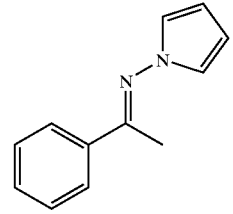

III.2

Yield: 89%, empirical formula: C$_{12}$H$_{12}$N$_2$, color: whiteish beige, m.p.: 61° C.

1H NMR (CDCl$_3$): 2.43 (3H, s, CH$_3$); 6.25–7.95 (9H, m, phenyl, pyrrolyl)

13C NMR (CDCl$_3$): 16.7 (CH$_3$), 106.8, 118.2, 127.0, 128.5, 130.7, 137.3 (phenyl, pyrrolyl), 166.5 (C=N)

IR (KBr, cm$^{-1}$): 3132 (w), 1605 (s), 1573 (m), 1445 (m), 1306 (s), 1082 (vs), 1067 (s), 988 (s), 924 (m), 818 (m), 766 (s), 716 (vs), 688 (vs)

3rd method (from: B. Bildstein, et al. Synthesis 1994, 2, 157–160): 10.6 ml of 2,6-diisopropylaniline (106 mmol) were placed in a baked-out Schlen tube which had been flushed with argon and were dissolved in 50 ml of absolute toluene. After addition of trimethylaluminum (53 ml, 2.0 M solution in toluene, 1 equivalent based on diisopropylaniline), the foaming solution was stirred at 80°

C. for 90 minutes. After evolution of methane was no longer observed, the solution was cooled to room temperature and admixed with 6.2 ml of acetophenone (53 mmol) (immediate color change from light-yellow to yellow). After stirring at room temperature for ½ hour, the solution was cooled to 0° C. and carefully hydrolyzed with small amounts of water (a little at a time). The white Al(OH)$_3$ was washed away using 3 portions of 5% KOH. The organic phase was subsequently washed 3 times with H$_2$O, separated off and dried over Na$_2$SO$_4$. After removal of the desiccant by filtration, the solvent was distilled off on a rotary evaporator. The yellow, oily residue was admixed with hexane and placed in a freezer chest (−30° C.). The imine crystallized overnight.

This method was used to prepare the imines III.3 to III.6.

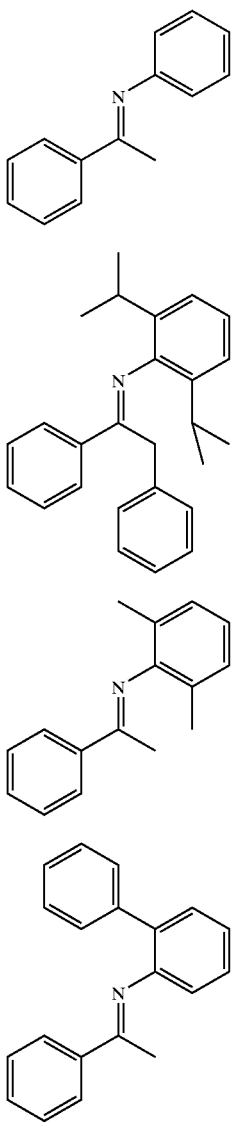

III.3

III.4

III.5

III.6

Imine III.3: yield: 36%, empirical formula: C$_{14}$H$_{13}$N, color: yellow

1H NMR (CDCl$_3$): 2.24 (3H, s, CH$_3$); 6.81–8.02 (10H, m, phenyl)

13C NMR (CDCl$_3$): 17.3 (CH$_3$); 115.0, 119.3, 123.1, 127.1, 128.3, 128.9, 129.2, 130.4, 139.4, 151.6 (phenyl); 165.4 (C=N)

IR (KBr, cm$^{-1}$): 1629 (s), 1592 (s), 1576 (m), 1447 (m), 1289 (m), 1214 (s), 1075 (s), 1025 (s), 909 (m), 812 (m), 783 (s), 760 (vs), 733 (s), 693 (vs)

The data agree with the literature data: A. Cobas et al., J. Org. Chem. 1993, 58, 3113–3117; M. Sato, et al., Chem. Lett. 1992, 3, 485; Reddelien, Chem. Ber. 1910, 43, 2478.

Imine III.4: yield: 73%, empirical formula: C$_{26}$H$_{29}$N, color: lemon yellow, m.p.: 82–83° C.

1H NMR (CDCl$_3$): 1.07 (6H, d, CH$_3$- phenyl), 1.04 (6H, d, CH$_3$-phenyl), 2.66 (2H, sept, CH); 3.84 (2H, s, CH$_2$); 6.80–7.92 (13H, m, phenyl)

13C NMR (CDCl$_3$):22.0, 23.7, 28.3, 36.8, 122.8, 123.5, 126.1, 128.1, 128.3, 128.4, 128.9, 130.1, 136.0, 136.2, 138.6, 146.0 (phenyl), 165.8 (C=N)

IR (KBr, cm$^{-1}$): 3066 (m), 3035 (w), 2962 (m), 2931 (m), 2867 (m), 1626 (vs), 1576 (s), 1497 (m), 1447 (s), 1431 (s), 1362 (m), 1297 (m), 1237 (m), 1192 (s), 1023 (m), 826 (m), 785 (vs), 768 (vs), 749 (s), 733 (vs), 698 (vs)

Imine III.5: yield: 42%, empirical formula: C$_{16}$H$_{17}$N, color: yellow

1H NMR (CDCl$_3$): 1.96 (6H, s, 2×CH$_3$); 1.99 (3H, s, CH$_3$), 6.82–7.97 (8H, m, phenyl)

13C NMR (CDCl$_3$): 17.4 (CH$_3$), 17.9 (2×CH$_3$), 117.9, 121.5, 122.7, 125.6, 127.0, 127.7, 128.1, 128.3, 130.4, 139.0, 148.9 (phenyl), 165.1 (C=N)

The data agree with the literature data: P. Schnider et al. Chem. Eur. J. 1997, 3, 887.

Imine III.6: yield: 51%, empirical formula: C$_{20}$H$_{17}$N, color: beige, m.p.: 57–58° C.

1H NMR (CDCl$_3$): 2.03 (3H, s, CH$_3$); 6.86–7.50 (14H, m, phenyl)

13C NMR (CDCl$_3$): 18.0 (CH$_3$), 119.9, 123.7, 126.5, 127.0, 127.9, 128.0, 128.2, 129.1, 130.2, 130.3, 131.7, 139.4, 139.9, 149.1 (phenyl), 165.3 (C=N)

IR (KBr, cm$^{-1}$): 3056 (w), 3018 (w), 1652 (m), 1636 (vs), 1596 (m), 1578 (m), 1472 (s), 1447 (s), 1432 (m), 1362 (s), 1291 (s), 1241 (s), 1113 (m), 1075 (m), 1025 (m), 920 (m), 824 (m), 787 (m), 776 (m), 760 (vs), 747 (vs), 702 (vs), 691 (vs) M$^+$=271.2 m/e 1.2. Synthesis of the Ligands of the Formula II General Procedure Using Ligand II.1 as an Example 0.18 ml of diisopropylamine (1.3 mmol) was placed in a baked-out Schlenk tube which had been flushed with argon, dissolved in 10 ml of THF (absolute) and admixed at −80° C. with n-BuLi (0.72 ml, 1.1 equivalents, 2.0 M solution in pentane). After removal of the cold bath (EtOH, N$_2$), the LDA solution formed was stirred at room temperature for ½ hour.

The imine III.1 (0.36 g, 1.30 mmol) was added to the freshly prepared LDA solution at −80° C. After removal of the cold bath, the dissolved starting material was stirred at room temperature for 2 hours and thereby deprotonated (color change: yellowish to yellowish green).

0.24 g of benzophenone (1.3 mmol) were subsequently added at room temperature and stirred overnight.

The yellow THF solution was then poured into 100 ml of ice water and extracted 3 times with 25 ml each time of diethyl ether. The combined organic phases were washed with H$_2$O, dried over Na$_2$SO$_4$ and the organic solvents were removed on a rotary evaporator. The yellow product crystallized over a period of 2 hours. Subsequent recrystallization from ethyl acetate/hexane gave the pure β-hydroxyimine.

This method was used to prepare the following β-hydroxyimines II.1–8:

Ligand II.1

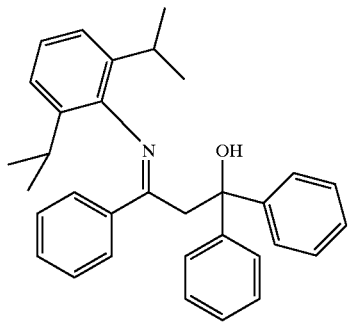

Yield: 72%, empirical formula: $C_{33}H_{35}NO$, color: whiteish yellow, m.p.: 121–122° C.

1H NMR (CDCl$_3$): 0.61 (6H, d, 2×CH$_3$), 0.82 (6H, d, 2×CH$_3$), 2.19 (2H, sept, CH), 3.76 (2H, s, CH$_2$), 6.80–7.51 (19H, m, phenyl, OH)

13C NMR (CDCl$_3$): 22.0, 24.5, 27.9 (CH$_3$, CH), 48.4 (CH$_2$), 78.5 (C—OH), 122.9, 124.2, 126.0, 126.7, 127.0, 128.1, 128.2, 128.3, 129.5, 130.0, 132.4, 136.8, 137.6, 143.6, 147.4 (phenyl), 170.4 (C=N)

IR (KBr, cm$^{-1}$): 3288 (m, broad), 3062 (w), 2962 (m), 2925 (w), 2867 (m), 1634 (vs), 1492 (m), 1453 (vs), 1343 (m), 1227 (m), 1065 (m), 1042 (s), 1015 (s), 942 (s), 917 (m), 899 (s), 805 (m), 749 (vs), 700 (vs), 637 (s).

M$^+$=461.3 m/e

Ligand II.2:

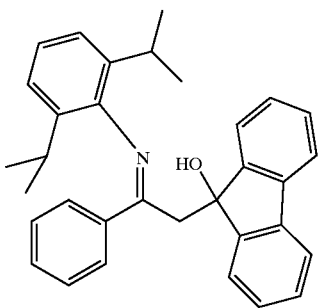

Yield: 96%, empirical formula: $C_{33}H_{33}NO$, color: light yellow, m.p.: 92–94° C.

1H NMR (CDCl$_3$): 0.76 (3H, d, CH$_3$), 1.07 (3H, d, CH$_3$), 1.09 (3H, d, CH$_3$), 1.16 (3H, s, CH$_3$), 2.69, 2.85 (2H, 2×sept, 2×CH), 3.44 (2H, s, CH$_2$), 6.85–7.98 (16H, m, phenyl, fluorenyl)

13C NMR (CDCl$_3$): 22.3, 22.9, 23.2, 24.8, 28.2, 28.3 (2×CH, 4×CH$_3$), 47.9 (CH$_2$), 81.6 (C—OH), 119.9, 120.2, 122.9, 123.2, 123.3, 124.2, 124.5, 124.6, 127.1, 127.7, 128.0, 128.4, 128.8, 129.0, 129.4, 130.3, 134.6, 136.0, 136.8, 139.4, 149.3 (phenyl, fluorenyl), 170.0 (C=N)

IR (KBr, cm$^{-1}$): 3305 (m, broad), 3066 (w), 3022 (w), 2962 (m), 2925 (m), 2865 (m), 1646 (s), 1623 (s), 1589 (m), 1451 (vs), 1381 (m), 1360 (m), 1216 (m), 1069 (m), 1025 (vs), 1011 (s), 936 (m), 851 (m), 793 (s), 770 (vs), 762 (vs), 698 (vs)

Ligand II.3

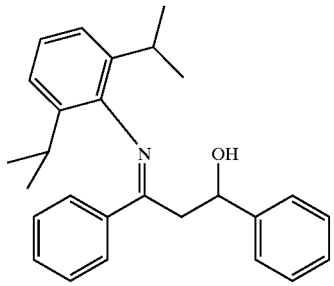

Yield: 59%, empirical formula: $C_{27}H_{31}NO$, color: white, m.p.: 69–71° C.

1H NMR (CDCl$_3$): 0.67–1.20 (m, 4×CH$_3$), 2.60, 2.88 (2×sept, CH), 6.58–7.70 (m, phenyl)

IR (KBr, cm$^{-1}$): 3247 (m, broad, OH), 3064 (w), 3033 (w), 2958 (s), 1632 (vs), 1457 (s), 1320 (m), 1299 (m), 1184 (m), 1069 (s), 1025 (m), 822 (s), 764 (s), 700 (vs)

M$^+$=386.2 m/e

Ligand II.4

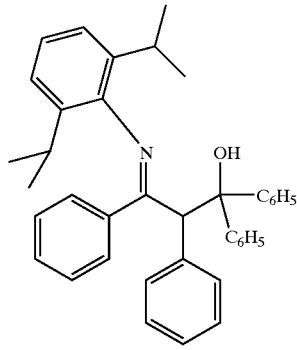

Yield: 72%, empirical formula: $C_{39}H_{39}NO$, color: white, m.p.: 165° C.

1H NMR (CDCl$_3$): 0.24 (3H, d, CH$_3$), 0.76 (3H, d, CH$_3$), 0.93 (3H, d, CH$_3$), 1.04 (3H, d, CH$_3$), 1.82 (1H, sept, CH), 2.48 (1H, sept, CH), 5.1 (1H, s, CH-phenyl), 6.81–7.70 (24H, m, phenyl, OH)

13C NMR (CDCl$_3$): 21.6, 22.1, 24.9, 25.0 (4×CH$_3$), 27.0, 27.7 (2×CH), 61.1 (CH-phenyl), 82.3 (C—OH), 122.5, 123.6, 124.4, 125.9, 126.0, 126.9, 127.0, 127.1, 127.2, 127.5, 128.0, 128.1, 129.1, 131.0, 135.5, 136.1, 138.9, 139.4, 143.1, 145.1, 148.5 (phenyl), 173.8 (C=N)

IR (KBr, cm$^{-1}$): 3305 (m, broad), 3058 (w), 3027 (w), 2983 (m), 2956 (m), 2927 (w), 2867 (w), 1632 (vs), 1600 (m), 1493 (m), 1451 (s), 1439 (m), 1383 (m), 1328 (m), 1252 (m), 1219 (m), 1177 (m), 1063 (m), 1042 (m), 803 (m), 780 (m), 768 (s), 749 (s), 729 (s), 698 (vs)

Ligand II.5

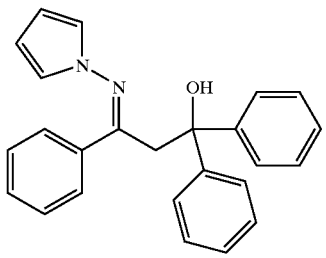

As a deviation from the general procedure, the THF solution of the ligand was not extracted with ether but instead firstly poured onto ice, then digested twice with 5 ml each time of hexane and refluxed for 10 minutes. After cooling, the ligand precipitated as a whiteish yellow powder.

Yield: 55%, empirical formula: $C_{25}H_{22}N_2O$, color: whiteish yellow, m.p.: 120–122° C.

1H NMR (CDCl$_3$): 3.67 (2H, s, CH$_2$), 5.92 (2H, t, pyrrolyl), 6.04 (1H, s, OH), 6.24 (2H, t, pyrrolyl), 7.0–7.54 (15H, m, phenyl)

13C NMR (CDCl$_3$): 49.1 (CH$_2$), 78.0 (C—OH), 106.8, 118.6, 125.9, 126.0, 126.8, 128.1, 129.0, 129.6, 136.6, 146.5, 164.6 (C=N)

IR (KBr, cm$^{-1}$): 3388 (s), 1611 (m), 1493 (s), 1464 (s), 1449 (s), 1400 (s), 1261 (m), 1246 (s), 1232 (m), 1178 (m), 1072 (s), 1014 (m), 964 (m), 939 (m), 904 (m), 772 (s), 766 (s), 754 (s), 727 (s), 698 (s)

M$^+$=366.2 m/e

Ligand II.6:

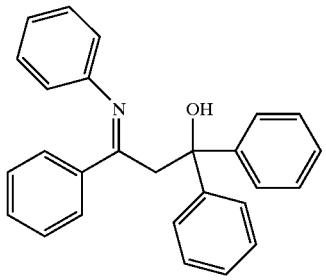

As a deviation from the general procedure, the THF solution of the ligand was not extracted with ether but instead firstly poured onto ice, then digested twice with 5 ml each time of hexane and refluxed for 10 minutes. After cooling, the ligand precipitated as a whiteish yellow powder.

Yield: 57%, empirical formula: $C_{27}H_{23}NO$, color: whiteish yellow

1H NMR (CDCl$_3$): 3.72 (2H, s, CH$_2$), 6.38–7.58 (21H, m, phenyl, OH)

13C NMR (CDCl$_3$): 49.3 (CH$_2$), 78.3 (C—OH), 120.8, 123.7, 126.1, 126.6, 127.1, 128.0, 128.1, 128.2, 128.3, 128.4, 128.8, 130.0, 132.4, 137.7, 147.0, 148.6 (phenyl), 171.7 (C=N)

IR (KBr, cm$^{-1}$): 3234 (broad), 3083 (w), 3058 (w), 3031 (w), 1638 (s), 1591 (s), 1489 (s), 1453 (s), 1430 (m), 1337 (m), 1229 (s), 1189 (m), 1177 (m), 1079 (m), 1063 (s), 1023 (m), 1015 (s), 940 (s), 909 (s), 778 (s), 753 (s), 739 (m), 700 (vs), 631 (s)

M$^+$=377.2 m/e

Ligand II.7

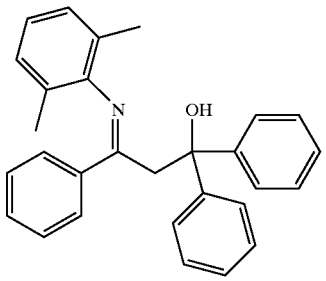

As a deviation from the general method, the ligand was recrystallized from diethyl ether.

Yield: 88%, empirical formula: $C_{29}H_{27}NO$, color: whiteish yellow, m.p.: 104–105° C. (Et$_2$O)

1H NMR (CDCl$_3$): 1.61 (6H, s, CH$_3$), 3.81 (2H, s, CH$_2$), 6.79–7.61 (19H, m, phenyl, OH)

13C NMR (CDCl$_3$): 17.8 (CH$_3$), 48.6 (CH$_2$), 78.3 (C—OH), 123.4, 126.0, 126.2, 126.5, 126.6, 127.7, 128.2, 129.5, 138.2, 146.6, 147.3 (phenyl), 170.5 (C=N)

IR (KBr, cm$^{31\ 1}$): 3305 (broad), 3060 (w), 3027 (w), 2968 (w), 2943 (w), 1640 (vs), 1594 (m), 1493 (m), 1451 (s), 1378 (m), 1347 (m), 1225 (m), 1200 (m), 1183 (m), 1065 (m), 1044 (m), 1013 (m), 940 (m), 903 (s), 776 (vs), 747 (s), 700 (vs), 633 (m)

M$^+$=405.54 m/e

Ligand II.8

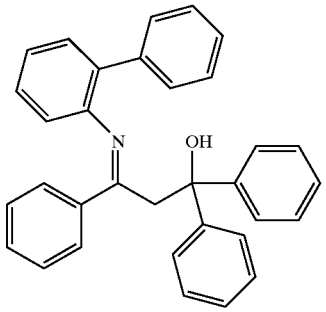

As a deviation from the general method, the ligand II.8 was recrystallized from diethyl ether/hexane.

Yield: 61%, empirical formula: $C_{33}H_{27}NO$, brown oil

1H NMR (CDCl$_3$): 3.43 (2H, s, CH$_2$), 6.27–7.73 (25H, m, phenyl+OH)

13C NMR (CDCl$_3$): 48.6 (CH$_2$), 78.1 (C—OH), 121.6, 124.3, 126.0, 126.5, 127.0, 127.5, 127.8, 127.9, 128.1, 128.2, 128.6, 128.9, 129.1, 130.0, 132.4, 132.5, 137.9, 139.4, 146.3, 147.1 (phenyl), 171.9 (C=N)

TABLE 1

Overview of the ligands of the formula II

| Ligand | R$^1$ | R$^2$ | R$^3$ | R$^4$ | R$^5$ | R$^6$ | Nu |
|---|---|---|---|---|---|---|---|
| II.1 | Ph | H | H | Ph | Ph | (C$_3$H$_8$)$_2$Ar | O |
| II.2 | Ph | H | H | 9,9-fluorenyl | | (C$_3$H$_8$)$_2$Ar | O |
| II.3 | Ph | H | H | H | Ph | (C$_3$H$_8$)$_2$Ar | O |
| II.4 | Ph | Ph | H | Ph | Ph | (C$_3$H$_8$)$_2$Ar | O |
| II.5 | Ph | H | H | Ph | Ph | N-pyrrolyl | O |
| II.6 | Ph | H | H | Ph | Ph | Ph | O |

TABLE 1-continued

Overview of the ligands of the formula II

| Ligand | R¹ | R² | R³ | R⁴ | R⁵ | R⁶ | Nu |
|---|---|---|---|---|---|---|---|
| II.7 | Ph | H | H | Ph | Ph | Me₂Ar | O |
| II.8 | Ph | H | H | Ph | Ph | Biphen | O |

Abbreviations:
Ph = phenyl,
$(C_3H_8)_2Ar$ = 2,6-diisopropylphenyl,
$Me_2Ar$ = 2,6-dimethylphenyl,
Biphen = ortho-biphenyl 2. Synthesis of Selected Complexes of the Formulae Ia and Ib General Procedure Using the Complex I.b.1 as an Example The ligand II.1 (1.07 g, 2.32 mmol) was placed in a baked-out Schlenk tube which had been flushed with argon, dissolved in 20 ml of THF (absolute) and deprotonated by means of n-BuLi (1.2 ml, 2.4 mmol, 2.0 M in pentane) while cooling to −80° C. in a cold bath (EtOH, N₂). After removal of the cold bath, the solution was stirred at room temperature for 1 hour (color change: yellow to light red).

After addition of the transition metal halide ($ZrCl_4$, 0.27 g, 1.12 mmol, 0.5 equivalent) at −80° C., the solution was warmed over a period of 1 hour and became dark red. It was stirred for 18 hours.

The THF was subsequently distilled off in a high vacuum and the orange-brown residue was suspended in 50 ml of toluene (absolute). The LiCl formed in the reaction was removed from the suspension by filtration. The solution was subsequently evaporated to dryness in a high vacuum, and the residue was digested and washed 3 times with 10 ml of hexane (absolute). The solvent was siphoned off and the pulverulent, orange complex I.b.1 was dried in a high vacuum.

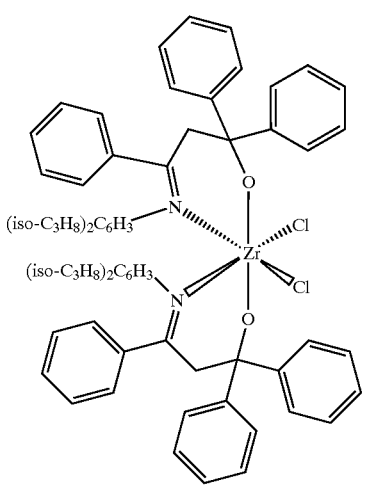

I.b.1

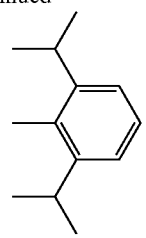

$(iso-C_3H_8)_2C_6H_3 =$

Complex I.b.1

Yield: 39%, empirical formula: $C_{66}H_{68}Cl_2N_2O_2Zr$, color: orange

1H NMR (d₆-benzene): 1.11, 1.29 (12H, 2 xd, 4×CH₃, J=6.6 Hz), 1.17, 1.26 (12H, 2×d, 4×CH₃, J=7.4 Hz), 1.80 (4H, s, 2×CH₂), 2.87, 3.28 (4H, 2×sept, 4×CH), 6.71–8.02 (36H, m, phenyl)

MS: $(LH_2^++LH)$—$ZrCl_2$=923.7 m/e, $(LH_2^++LH-H_2O)$—$ZrCl_2$=905.7 m/e, L=ligand Complex I.a.1

General remark:

Each of the complexes of the formula Ia was synthesized using 1 equivalent of $MCl_4$, based on the ligand of the formula II.

Yield: 49%, empirical formula: $C_{33}H_{34}Cl_3NOZr$, color: orange-brown

1H NMR (d₆-benzene): 1.10 (3H, d, CH₃, J=6.7 Hz), 1.18 (3H, d, CH₃, J=7.1 Hz), 1.21 (3H, d, CH₃, J=6.7 Hz), 1.36 (3H, d, CH₃, J=6.4 Hz), 1.85, 2.10 (2H, 2×s, CH₂, 2 isomers), 2.86, 3.33 (2H, 2×sept, 2×CH, 2 isomers), 6.57–8.08 (18H, m, phenyl)

Complex I.a.2

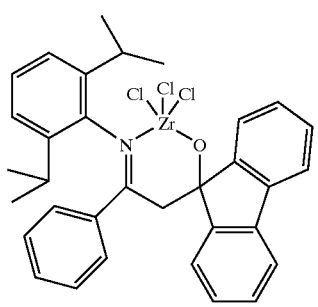

I.a.2

Yield: 67%, empirical formula: $C_{33}H_{32}Cl_3NOZr$, color: yellow

1H NMR (d₆-benzene): 0.90, 1.12 (6H, 2×d, 2×CH₃, J=6.9 Hz), 1.17, 1.21 (6H, 2×d, 2×CH₃, J=7.1 Hz), 1.85, 2.10 (2H, 2×s, CH₂, 2 isomers—ratio 1:2), 2.83, 3.21 (2H, 2×sept, 2×CH, 2 isomers in the ratio 1:2), 6.68–8.28 (16H, m, phenyl)

MS: $(L^+-H_2O)$=442.2 m/e, L: ligand

Elemental analysis found (calculated): C 59.4 (60.4); H 5.8 (4.9); N 1.4 (2.1)

Complex I.a.3

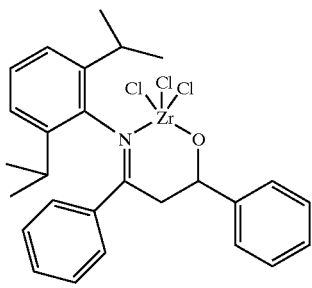

Yield: 52%, empirical formula: $C_{27}H_{30}Cl_3NOZr$, color: yellow

1H NMR ($d_6$-benzene): 0.88–1.42 (12H, 4×d, 4×$CH_3$), 1.80, 2.10 (2H, 2×s, $CH_2$, 2 isomers), 2.86–3.19 (1H, m, CH-phenyl), 3.56 (2H, $CH_2$), 6.81–8.02 (13H, m, phenyl)

MS: ($L^+-H_2O$)=368.3 m/e, L: ligand

Complex I.a.4

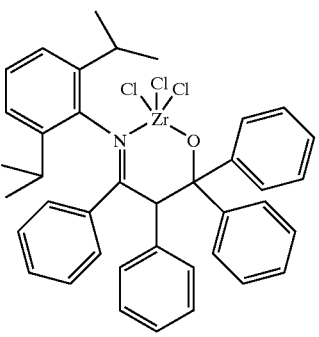

Yield: 49%, empirical formula: $C_{39}H_{38}Cl_3NOZr$, color: whiteish yellow

1H NMR ($d_6$-benzene): 0.73–1.26 (m), 0.27 (m), 6.73–8.23 (m)

Complex I.a.5

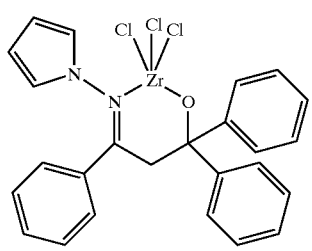

Yield: 50%, empirical formula: $C_{25}H_{21}Cl_3N_2OZr$, color: brick red

1H NMR ($CD_2Cl_2$): 2.34, 3.58 ($CH_2$, 2 isomers), 5.85 (pyrrole), 6.19 (pyrrole), 7.10–7.78 (m, aromatic)

MS: ($L^+-H_2O$)=349.2 m/e

Elemental analysis found (calculated): C 54.6 (53.3); H 4.6 (3.8); N 4.1 (5.0)

Complex I.a.6

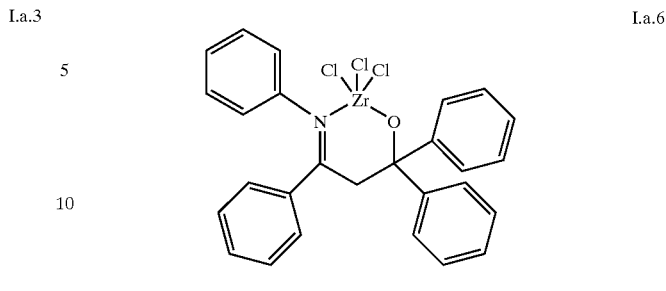

Yield: 82%, empirical formula: $C_{27}H_{22}Cl_3NOZr$, color: yellow

1H NMR ($CD_2Cl_2$): 2.29 ($CH_2$), 6.70–8.03 (m, phenyl)

MS: ($L^+-H_2O$)=360.2 m/e

Complex I.a.7

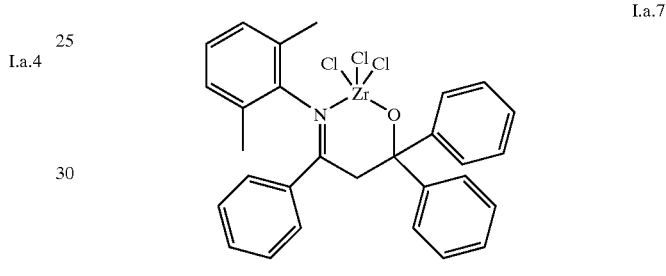

Yield: 63%, empirical formula: $C_{29}H_{26}Cl_3NOZr$, color: yellow

1H NMR ($CD_2Cl_2$): 2.08, 2.23, 2.39, 6.41, 6.99–8.14 (m, phenyl)

MS: ($M^+-ZrCl_3$)=406.3, ($L^+-H_2O$)=388.2 m/e

Complex I.a.8

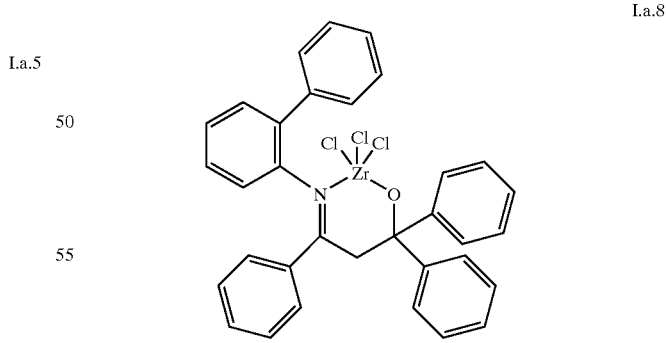

Yield: 71%, empirical formula: $C_{33}H_{26}Cl_3NOZr$, color: yellow

1H NMR ($CD_2Cl_2$): 3.67 (2H, s, $CH_2$), 5.92–7.85 (24H, m, phenyl)

MS: ($L^+-H_2O$)=463.25 m/e

Complex I.a.9

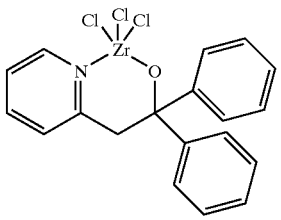

I.a.9

The ligand was synthesized by the method of Tilford, J. Am. Chem. Soc. 1954, 76, 2431 and ibid, 1954, 76, 2436.

Yield: 80%, empirical formula: $C_{19}H_{16}Cl_3NOZr$, color: light beige

1H NMR ($CD_2Cl_2$): 2.33, 6.73–7.59 (m), 9.18 (d), 9.40–9.46 (m)

Complex I.a.10

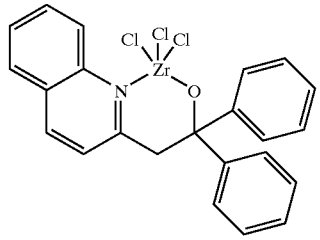

I.a.10

The ligand was synthesized by the method of Tilford, J. Am. Chem. Soc. 1954, 76, 2431 and ibid, 1954, 76, 2436.

Yield: 83%, empirical formula: $C_{23}H_{18}Cl_3NOZr$, color: lemon yellow

1H NMR ($CD_2Cl_2$): 1.88 (8H, s, 4×$CH_2$, 2 coordinated THF), 3.79 (10H, s, broad, 4×$CH_2$—O, 2 coordinated THF, $CH_2$, ligand), 6.80–8.36 (m, aromatic)

TABLE 2

Overview of the complexes of the formula I a

| Complex | $R^2$ | $R^3$ | $R^4$ | $R^5$ | $R^6$ | $R^1$ | M | Nu |
|---|---|---|---|---|---|---|---|---|
| I.a.1 | H | H | Ph | Ph | $(C_3H_8)_2Ar$ | Ph | Zr | O |
| I.a.2 | H | H | 9,9-fluorenyl | | $(C_3H_8)_2Ar$ | Ph | Zr | O |
| I.a.3 | H | H | H | Ph | $(C_3H_8)_2Ar$ | Ph | Zr | O |
| I.a.4 | Ph | H | Ph | Ph | $(C_3H_8)_2Ar$ | Ph | Zr | O |
| I.a.5 | H | H | Ph | Ph | N-pyrrolyl | Ph | Zr | O |
| I.a.6 | H | H | Ph | Ph | Ph | Ph | Zr | O |
| I.a.7 | H | H | Ph | Ph | $Me_2Ar$ | Ph | Zr | O |
| I.a.8 | H | H | Ph | Ph | Biphen | Ph | Zr | O |
| I.a.9 | H | H | Ph | Ph | —CH—CH=CH—CH— | | Zr | O |
| I.a.10 | H | H | Ph | Ph | —CH—CH=CH—CH—, substitutedd by —CH—CH=CH—CH— | | Zr | O |

Complex I.b.2

Yield: 51%, empirical formula: $C_{66}H_{64}Cl_2N_2O_2Zr$, color: orange

1H NMR ($d_6$-benzene): 0.96, 1.12 (6H, 2 xd, 2×$CH_3$, J=6.8 Hz), 0.99, 1.20 (6H, 2×d, 2×$CH_3$), 1.80 (4H, s, 2×$CH_2$), 2.87, 3.20 (4H, 2×sept, 4×CH), 6.68–8.28 (32H, m, phenyl)

MS: ($L^+$–$H_2O$)=441.2 m/e, L: ligand

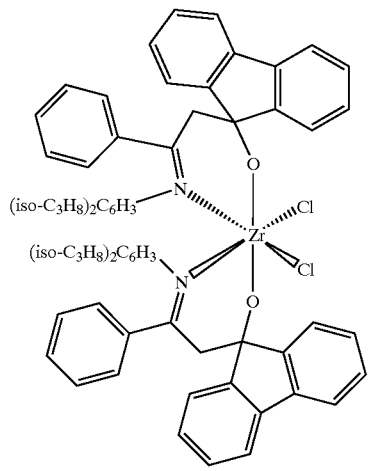

I.b.2

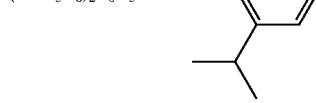

Complex I.b.3

Yield: 67%, empirical formula: $C_{54}H_{60}Cl_2N_2O_2Zr$, color: lemon yellow

1H NMR ($d_6$-benzene): 1.19 (d, $CH_3$), 1.23 (d, $CH_3$), 3.19 (sept, CH), 6.79–8.11 (m, phenyl)

MS: ($L^+$–$H_2O$)=368.3 m/e, L: ligand

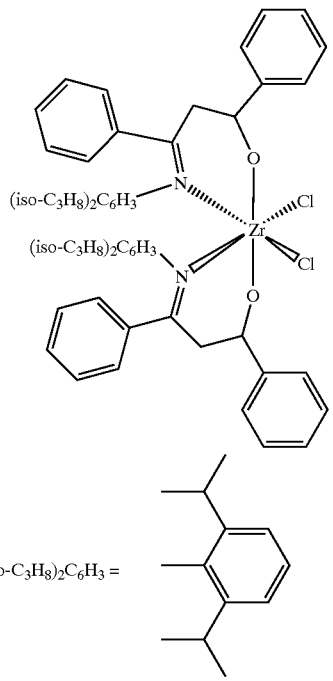

I.b.3

Complex I.b.4

Yield 86%, empirical formula: $C_{38}H_{32}Cl_2N_2O_2Zr$, color: light beige

1H NMR ($CD_2Cl_2$): 2.36, 6.71–7.38 (m), 8.54 (m).

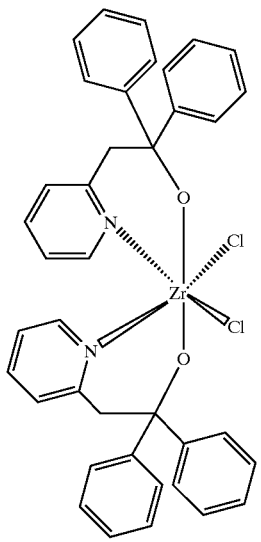

Complex I.b.5

Yield: 48%, empirical formula: $C_{46}H_{36}Cl_2N_2O_2Zr$, color: beige

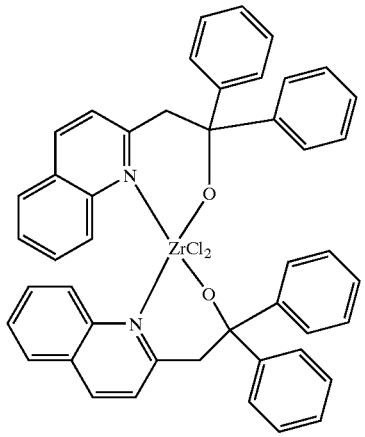

1H NMR ($CD_2Cl_2$): 1.81 (4H, s, 2×$CH_2$, 1 coordinated THF), 3.70 (6H, s, 2×$CH_2$—O, 1 coordinated THF, $CH_2$, ligand), 6.80–8.05 (m, aromatic)

Complex I.b.6

Yield: 71%, empirical formula: $C_{46}H_{36}Cl_2N_2O_2Ti$, color: light green

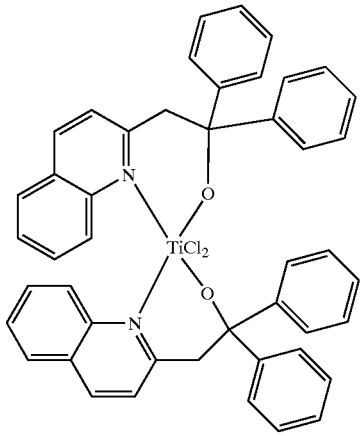

1H NMR ($CD_2Cl_2$): 1.31 (s), 1.87 (s, broad, THF), 3.72 (s, broad, THF), 6.59–8.09 (m, aromatic)

Complex I.b.7

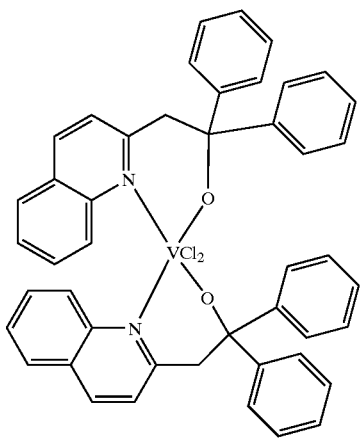

Yield: 53%, empirical formula: $C_{46}H_{36}Cl_2N_2O_2V$, color: brick red

1H NMR ($CD_2Cl_2$): paramagnetic, 2.0 (s, very broad), 7.5 (s, very broad)

TABLE 3

Overview of the complexes of the formula I b

| Complex | $R^2$ | $R^3$ | $R^4$ | $R^5$ | $R^6$ | $R^1$ | M | Nu |
|---|---|---|---|---|---|---|---|---|
| I.b.1 | H | H | Ph | Ph | $(C_3H_8)_2Ar$ | Ph | Zr | O |
| I.b.2 | H | H | 9,9-fluorenyl | | $(C_3H_8)_2Ar$ | Ph | Zr | O |
| I.b.3 | H | H | Ph | Ph | $(C_3H_8)_2Ar$ | Ph | Zr | O |
| I.b.4 | H | H | Ph | Ph | —CH=CH—CH=CH— | Ph | Zr | O |
| I.b.5 | H | H | Ph | Ph | —CH—CH=CH—CH, substituted by —CH=CH—CH=CH— | Ph | Zr | O |
| I.b.6 | H | H | Ph | Ph | —CH—CH=CH—CH, substituted by —CH=CH—CH=CH— | Ph | Ti | O |
| I.b.7 | H | H | Ph | Ph | —CH—CH=CH—CH, substituted by —CH=CH—CH=CH— | Ph | V | O |

3. Polymerization Experiments

3.1. Polymerization at Atmospheric Pressure

In a Schlenk tube which had been made inert, a solution composed of 20 mg of the complex to be examined, 1 ml of 30% strength by weight MAO solution (in toluene) and 50 ml of toluene was prepared. This reaction mixture was, unless indicated otherwise, stirred under an ethylene atmosphere for 90 minutes at room temperature. The precipitated white solid was filtered off, the solid was washed with methanol and dried under reduced pressure. The polymer was obtained in the form of a white powder.

3.2. Polymerization in an Autoclave 20 mg of the complex to be examined, 2 ml of 30% strength by weight MAO solution in toluene and 400 ml of toluene were placed in a 1 l steel autoclave which had been made inert. At 70° C., the autoclave was pressurized with ethylene to a pressure of 40 bar. This pressure was kept constant during the 90 minute duration of the experiment by introduction of further ethylene. The reaction was stopped by venting and the polymer was isolated by filtration, subsequent washing with methanol and drying under reduced pressure.

3.3. Copolymerization of Ethylene/hexene

The procedure of 3.2. was repeated, but 20 ml of 1-hexene were placed in the autoclave at the beginning together with the other reagents.

3.4. Polymerization Using Hydrogen as Molar Mass Regulator

The procedure of 3.2. was repeated, but 4 l of hydrogen (at STP) are introduced into the autoclave at the beginning.

The results are summarized in Table 4.

TABLE 4

Polymerization results obtained using complexes of the formula I.a

| Complex | Polymerization of ethylene at atmospheric pressure Yield [g] | η value [dl/g] | Polymerization of ethylene at 40 bar Yield [g] | η value [dl/g] | Copolymerization of ethylene/hexene Yield [g] | η value [dl/g] | Hexene content of copolymer [% by weight] | Influence of hydrogen on the polymerization of ethylene Yield [g] | η value [dl/g] |
|---|---|---|---|---|---|---|---|---|---|
| I.a.1 | 1.3 | 40.2 | 11.0 | 42.0 | | | | | |
| I.a.2 | | | 19.2 | 51.9 | 23.0 | 36.5 | <0.6 | 9.7 | 12.6 |
| I.a.3 | 1.3 | 28.8 | 15.6 | 13.6 | | | | | |
| I.a.4 | 1.5 | 20.4 | 23.6 | 41.1 | | | | | |
| I.a.5 | 1.6 | 31.4 | 24.1 | 51.4 | | | | | |
| I.a.6 | 2.4 | 27.0 | 30.7 | 20.6 | | | | | |
| I.a.7 | 2.4 | 36.8 | 34.3 | 33.8 | | | | | |
| I.a.8 | 2.8 | 30.8 | 33.3 | 27.5 | | | | | |
| I.a.9 | 1.9 | 36.7 | 28.5 | 67.3 | 23.0 | 20.0 | 1.6 | 39.3 | 15.5 |
| I.a.10 | 1.2* | 65.4 | 31.6 | 24.6 | 30.7 | 22.0 | <0.8 | | |

*Polymerization time of 120 minutes

TABLE 5

Polymerization results obtained using complexes of the formula I.b

| Complex | Polymerization of ethylene at atmospheric pressure Yield [g] | η value [dl/g] | Polymerization of ethylene at 40 bar Yield [g] | η value [dl/g] | Copolymerization of ethylene/hexene Yield [g] | η value [dl/g] | Hexene content of copolymer [% by weight] | Influence of hydrogen on the polymerization of ethylene Yield [g] | η value [dl/g] |
|---|---|---|---|---|---|---|---|---|---|
| I.b.1 | | | 22.0 | | | | | | |
| I.b.2 | | | 0.9 | 24.3 | | | | | |
| I.b.3 | | | 2.9 | 13.7 | | | | | |
| I.b.4 | | | 0.1 | 45.6 | | | | | |
| I.b.5 | 0.6 | 21.2 | 29.2 | 46.8 | 20.7 | 30.1 | <0.6 | 18.1 | 9.4 |
| I.b.6 | 0.4 | 19.5 | 24.5 | 38.7 | 15.2 | 41.9 | 1.3 | 2.4 | 16.3 |
| I.b.7 | 0.3 | 24.6 | 40.0 | 46.1 | 43.4 | 26.6 | <0.8 | 15.5 | 4.5 |

We claim:

1. A complex of the formula Ia or Ib,

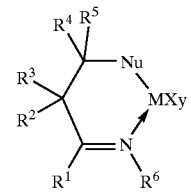

Ia

-continued

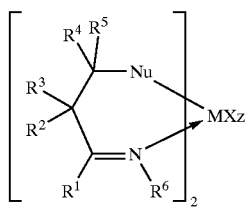

where the variables are defined as follows:

Nu is selected from the group consisting O, S and N—$R^7$;

M is selected from the group consisting Ti, Zr, Hf, V, Nb and Ta;

y corresponds to the oxidation state of M minus 1;

z corresponds to the oxidation state of M minus 2;

X are identical or different and are selected from the group consisting of a halogen, $C_1$–$C_8$-alkyl, $C_3$–$C_{12}$-cycloalkyl, $C_7$–$C_{13}$-aralkyl, and a $C_6$–$C_{14}$-aryl, $R^1$ to $R^7$ are identical or different and are selected from the group consisting of a hydrogen, a substituted $C_1$–$C_{18}$-alkyl, an unsubstituted $C_1$–$C_{18}$ alkyl, a substituted $C_2$–$C_{18}$ alkenyl having from one to 4 isolated or conjugated double bonds, an unsubstituted $C_2$–$C_{18}$ alkenyl having from one to 4 isolated or conjugated double bonds, a substituted $C_3$–$C_{12}$-cycloalkyl, an unsubstituted $C_3$–$C_{12}$-cycloalkyl, a $C_7$–$C_{13}$-aralkyl, an unsubstituted $C_6$–$C_{14}$-aryl, a substituted $C_6$–$C_{14}$-aryl, wherein the substituted $C_6$–$C_{14}$-aryl has one or more identical or different substituents selected from the group consisting of a substituted $C_1$–$C_{18}$-alkyl, an unsubstituted $C_1$–$C_{18}$-alkyl, a substituted $C_1$–$C_{18}$-alkenyl, an unsubstituted $C_1$–$C_{18}$-alkenyl, a $C_3$–$C_{12}$-cycloalkyl, a $C_7$–$C_{13}$-aralkyl, a $C_6$–$C_{14}$-aryl, a halogen, a substituted $C_1$–$C_6$-alkoxy, an unsubstituted $C_1$–$C_6$-alkoxy, a $C_6$–$C_{14}$-aryloxy, a $SiR^8R^9R^{10}$, and O—$SiR^8R^9R^{10}$;

an unsubstituted five-membered nitrogen-containing heteroaryl radical, a substituted five-membered nitrogen-containing heteroaryl radical, an unsubstituted six-membered nitrogen-containing heteroaryl radical, and a substituted six-membered nitrogen-containing heteroaryl radical; wherein one or more substituents are identical or different and are selected from the group consisting of a substituted $C_1$–$C_{18}$-alkyl, an unsubstituted $C_1$–$C_{18}$-alkyl, a substituted $C_2$–$C_{18}$-alkenyl, an unsubstituted $C_2$–$C_{18}$-alkenyl, a $C_3$–$C_{12}$-cycloalkyl, a $C_7$–$C_{13}$-aralkyl, a $C_6$–$C_{14}$-aryl, a halogen, a $C_1$–$C_6$-alkoxy, a $C_6$–$C_{14}$-aryloxy, a $SiR^8R^9R^{10}$, or O—$SiR^8R^9R^{10}$;

where adjacent radicals $R^1$ to $R^5$ may be joined to one another or to $R^7$ to form a 5-membered to 12-membered non-aromatic ring and adjacent radicals $R^1$ and $R^6$ may be joined to one another to form a 5-membered to 12-membered ring, which 5-membered to 12-membered rings may in turn bear substituents selected from the group consisting of a substituted $C_1$–$C_8$-alkyl, an unsubstituted $C_1$–$C_8$-alkyl, a substituted $C_2$–$C_8$-alkenyl, an unsubstituted $C_2$–$C_8$-alkenyl and having from one to 4 isolated or conjugated double bonds, a substituted $C_3$–$C_{12}$-cycloalkyl, an unsubstituted $C_3$–$C_{12}$-cycloalkyl, a $C_7$–$C_{13}$-aralkyl, and a $C_6$–$C_{14}$-aryl;

$R^8$ to $R^{10}$ are identical or different and are selected from the group consisting of a hydrogen, a $C_1$–$C_8$-alkyl, a $C_3$–$C_{12}$-cycloalkyl, a $C_7$–$C_{13}$-aralkyl, and a $C_6$–$C_{14}$-aryl.

2. A complex as claimed in claim 1, wherein Nu is oxygen, and M is selected from the group consisting of Ti and Zr, and X is a halogen.

3. A process for the polymerization or copolymerization of an olefin, which comprises:

contacting a complex of the formula Ia or Ib as claimed in claim 1 with an olefin.

4. A process for preparing a complex as claimed in claim 1, which comprises:

deprotonating a ligand of the formula II

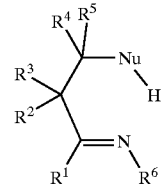

by means of a base; and subsequently reacting the product with a metal compound $MX_{y+1}$, where M is selected from the group consisting of Ti, Zr, Hf, V, Nb, and Ta, and X is selected from the group consisting of a halogen, a $C_1$–$C_8$-alkyl, a $C_3$–$C_{12}$-cycloalkyl, a $C_7$–$C_{13}$-aralkyl, and a $C_6$–$C_{14}$-aryl, where $MX_{y+1}$ may optionally be stabilized by uncharged ligands.

5. A process for preparing a supported catalyst for the polymerization or copolymerization of olefins, which comprises:

depositing one or more complexes as claimed in claim 1 and optionally an activator on a solid support.

6. A supported catalyst for the polymerization or copolymerization of olefins which is obtainable by a process as claimed in claim 5.

7. A process for the polymerization or copolymerization of olefins which comprises:

contacting a supported catalyst as claimed in claim 6, with an olefin.

8. A process as claimed in claim 3, further comprising:

contacting a complex of the formula Ia or Ib with an activator.

9. A process for the polymerization or copolymerization of olefins, which comprises:

contacting a complex of the formula Ia or Ib as claimed in claim 2 with an olefin.

10. A process for the polymerization or copolymerization of olefins as claimed in claim 9, further comprising contacting a complex of the formula Ia or Ib with an activator.

11. A process for preparing a complex as claimed in claim 2, which comprises:

deprotonating a ligand of the formula II

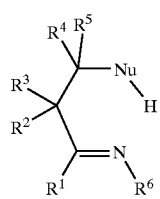

II by means of a base; and reacting the product with a metal compound $MX_{y+1}$; wherein M is selected from the group consisting of Ti, Zr, Hf, V, Nb, and Ta; and X is selected from the group consisting of a halogen, a $C_1$–$C_8$-alkyl, a $C_3$–$C_{12}$-cycloalkyl, a $C_7$–$C_{13}$-aralkyl, and a $C_6$–$C_{14}$-aryl, wherein $MX_{y+1}$ may optionally be stabilized by uncharged ligands.

12. A process for preparing a supported catalyst for the polymerization or copolymerization of olefins, which comprises:

depositing one or more complexes as claimed in claim 2 and optionally an activator on a solid support.

13. A process for polymerizing or copolymerizing olefins, which comprises;

contacting the supported catalyst obtained by the process as claimed in claim 6 with an olefin.

* * * * *